US010304374B2

(12) United States Patent
Di Sessa et al.

(10) Patent No.: US 10,304,374 B2
(45) Date of Patent: May 28, 2019

(54) MEDICAL APPARATUSES WITH SELECTIVELY DIMMABLE DISPLAYS

(71) Applicant: Azena Medical, LLC, Walnut Creek, CA (US)

(72) Inventors: Alexandre B. Di Sessa, Walnut Creek, CA (US); Jonathan Z. Luo, San Ramon, CA (US); Roberto Minoru Imai, Jr., Dublin, CA (US); Kenneth Lester Blanchard, Vacaville, CA (US)

(73) Assignee: Azena Medical, LLC, Walnut Creek, CA (US)

( * ) Notice: Subject to any disclaimer, the term of this patent is extended or adjusted under 35 U.S.C. 154(b) by 236 days.

(21) Appl. No.: 15/357,995

(22) Filed: Nov. 21, 2016

(65) Prior Publication Data

US 2017/0148378 A1 May 25, 2017

Related U.S. Application Data

(60) Provisional application No. 62/259,025, filed on Nov. 23, 2015.

(51) Int. Cl.
*G09G 3/30* (2006.01)
*A61B 18/22* (2006.01)
(Continued)

(52) U.S. Cl.
CPC .............. *G09G 3/30* (2013.01); *G06F 3/048* (2013.01); *A61B 18/22* (2013.01); *A61B 2017/0019* (2013.01); *A61B 2017/00199* (2013.01); *A61B 2018/2255* (2013.01); *A61B 2090/372* (2016.02); *A61C 1/0046* (2013.01); *A61N 2005/063* (2013.01);
(Continued)

(58) Field of Classification Search
CPC ............ A61B 18/22; A61B 2017/0019; A61B 2017/00199; A61B 2018/2255; A61B 2090/372; A61C 1/0046; A61N 2005/0606; A61N 2005/0626; A61N 2005/063; A61N 2005/0644; A61N 2005/067; G06F 3/048; G09G 2320/064; G09G 2320/0686; G09G 2370/08; G09G 2380/08; G09G 3/30; G02B 6/0006
See application file for complete search history.

(56) References Cited

U.S. PATENT DOCUMENTS

2004/0070195 A1* 4/2004 Nelson ................... B42D 3/123
283/83
2008/0276192 A1* 11/2008 Jones ................... A61C 1/0015
715/772

(Continued)

*Primary Examiner* — Afroza Chowdhury
(74) *Attorney, Agent, or Firm* — Carr & Ferrell LLP (57) ABSTRACT

Medical apparatuses with selectively dimmable displays are disclosed herein. Some embodiments include a housing, a laser surgical handpiece device, a laser source that generates laser light that is emitted through the laser surgical handpiece device, an electroluminescent display associated with the housing, the electroluminescent display being configured to display operational settings for the laser source, the operational settings including at least power level and pulse width or duration, and a microprocessor for controlling the electroluminescent display to selectively illuminate or dim at least a portion of the operational settings displayed thereon based on the operational settings selected by a user.

19 Claims, 10 Drawing Sheets

(51) Int. Cl.
*A61C 1/00* (2006.01)
*G06F 3/048* (2013.01)
*F21V 8/00* (2006.01)
*A61B 17/00* (2006.01)
*A61N 5/067* (2006.01)
*A61N 5/06* (2006.01)
*A61B 90/00* (2016.01)

(52) U.S. Cl.
CPC ............... *A61N 2005/0606* (2013.01); *A61N 2005/067* (2013.01); *A61N 2005/0626* (2013.01); *A61N 2005/0644* (2013.01); *G02B 6/0006* (2013.01); *G09G 2320/064* (2013.01); *G09G 2320/0686* (2013.01); *G09G 2370/08* (2013.01); *G09G 2380/08* (2013.01)

(56) References Cited

U.S. PATENT DOCUMENTS

| | | | | |
|---|---|---|---|---|
| 2009/0225060 A1* | 9/2009 | Rizoiu | ............... | A61C 1/0015 345/176 |
| 2009/0292168 A1* | 11/2009 | Farr | .................... | A61B 1/0607 600/109 |
| 2010/0299978 A1* | 12/2010 | Werners | ............ | B32B 17/10174 40/204 |
| 2011/0139851 A1* | 6/2011 | McCuen | .......... | A61B 17/07207 227/175.1 |
| 2015/0230865 A1* | 8/2015 | Sivriver | ................ | A61B 18/22 427/554 |

* cited by examiner

┌─────────────────────────────────────────────────────────────────────┐
│  Displaying selectable procedure options that correspond to a plurality of │
│     operational modes that each comprises unique combinations of    │
│          operational settings for a specific medical procedure      │
│                                  502                                │
└─────────────────────────────────────────────────────────────────────┘
                                    │
                                    ▼
┌─────────────────────────────────────────────────────────────────────┐
│    Receiving user input such as a user scrolling through the plurality of │
│     operational modes using inputs on the control panel or display  │
│                                  504                                │
└─────────────────────────────────────────────────────────────────────┘
                                    │
                                    ▼
┌─────────────────────────────────────────────────────────────────────┐
│        Displaying a preview of selected operational settings on the │
│                        electroluminescent display                   │
│                                  506                                │
└─────────────────────────────────────────────────────────────────────┘
                                    │
                                    ▼
┌─────────────────────────────────────────────────────────────────────┐
│  Selectively adjusting the power level of the laser device based on touch- │
│            based input received by the selectable dial indicator    │
│                                  508                                │
└─────────────────────────────────────────────────────────────────────┘
                                    │
                                    ▼
┌─────────────────────────────────────────────────────────────────────┐
│  Selectively illuminating a portion of the power indicator dial increments │
│     that correspond to the power level at a first luminance level, while │
│     remaining power indicator dial increments are not illuminated or are │
│     illuminated with a second luminance level that is less than the first │
│                             luminance level                         │
│                                  510                                │
└─────────────────────────────────────────────────────────────────────┘
```

```
    for (int a=0;a<36;a++) // We only use 36 of the 40 available
channels on each EL driver chip
    {
      if (a==0)
      {
        ClearPulse();
        DATARESET_1; // if it is the first pulse, we set data pin to let
it scan through the 40 channels
      }
      CLOCK_1;
      if (firstcycle)
      {
        if (a%2==0) // First cycle has positive pulses on even row
        {
          PositivePulse();
        }
        else
        {
          NegativePulse();
        }
      }
      else
      {
        if (a%2==0) // Second cycle has negative pulses on even row
        {
          NegativePulse();
        }
        else
        {
          PositivePulse();
        }
      }
      CLOCK_0;
      DATARESET_0;
      // For each loop, we send one clock pulse to move the data bit
through each channel.
    }
    for (int a=0;a<4;a++) // Clock through the remaining channels
    {
      CLOCK_1;
      CLOCK_0;
    }
    if (firstcycle)
    {
      firstcycle=false;
    }
    else
    {
      firstcycle=true;
      dimcycle++;
    }
    if (dimcycle==6 ) dimcycle=0; // We only send pulses to dimmed
channels every 6 cycles.
```

MEDICAL APPARATUSES WITH SELECTIVELY DIMMABLE DISPLAYS

CROSS REFERENCE TO RELATED APPLICATIONS

This application claims the benefit and priority of U.S. Provisional Application Ser. No. 62/259,025, filed on Nov. 23, 2015, which is hereby incorporated by reference herein including all references and appendices cited therein.

FIELD OF THE INVENTION

The present technology is directed to medical devices, and more particularly, but not by way of limitation, to apparatuses that comprise selectively dimmable and transparent displays. Methods for controlling the selective dimming of the displays and laser pulse control and selection are also provided herein.

SUMMARY

According to some embodiments, the present disclosure is directed to an apparatus, comprising: (a) a housing; (b) a laser surgical handpiece device; (c) a laser source that generates laser light that is emitted through the laser surgical handpiece device; (d) an electroluminescent display associated with the housing, the electroluminescent display being configured to display operational settings for the laser source, the operational settings comprising at least power level and pulse width or duration; and (e) a microprocessor for controlling the electroluminescent display to selectively illuminate or dim at least a portion of the operational settings displayed thereon based on the operational settings selected by a user.

According to some embodiments, the present disclosure is directed to a method, comprising: (a) displaying selectable procedure options that correspond to a plurality of operational modes that each comprises unique combinations of operational settings for a specific medical procedure; (b) receiving user input such as a user scrolling through the plurality of operational modes using inputs on the control panel (or in a touch-based selectable dial indicator displayed on the electroluminescent display); (c) displaying a preview of selected operational settings on the electroluminescent display; and (d) selectively adjusting the power level of the laser source based on touch-based input received by the selectable dial indicator.

According to some embodiments, the present disclosure is directed to a method, comprising: (a) addressing each of the traces/plurality of light emitting segments such that the microprocessor can send pulses to teach of the traces and therefore into the plurality of light emitting segments; (b) receiving user input such as a selection of an operation mode/setting or user input on the electroluminescent display; (c) selectively adjusting a luminance of the plurality of light emitting segments by applying positive and negative pulses at a specific voltage and at a frequency to selected traces; (d) selectively dimming the plurality of light emitting segments using a pulse skipping scheme; and (e) pulse skipping in subsequent cycles, which changes a frequency of energy pulses resulting in a portion of the light emitting segments being dimmer as more pulses are skipped.

BRIEF DESCRIPTION OF THE DRAWINGS

Certain embodiments of the present technology are illustrated by the accompanying figures. It will be understood that the figures are not necessarily to scale and that details not necessary for an understanding of the technology or that render other details difficult to perceive may be omitted. It will be understood that the technology is not necessarily limited to the particular embodiments illustrated herein.

DETAILED DESCRIPTION

Generally, the present disclosure includes medical apparatuses that include selectively dimmable displays. Example medical apparatuses include laser pulse devices used for dental procedures that involve teeth and gum cleaning, as well as oral surgical intervention and repair.

These apparatuses include selectively dimmable displays, which include, but are not limited to electroluminescent displays. In some embodiments, the electroluminescent displays include transparent displays that are selectively controlled to display selectable laser power and/or laser pulse settings for operating a pulsed laser. In some embodiments, the laser power settings can be associated with specific dental procedures such as frenectomy, gingivectomy, molar exposure, and tooth whitening—just to name a few. To be sure, the apparatuses can utilize selective control of laser power and laser pulse width and/or pulse timing to allow the user to perform various dental procedures.

Figure 1A:
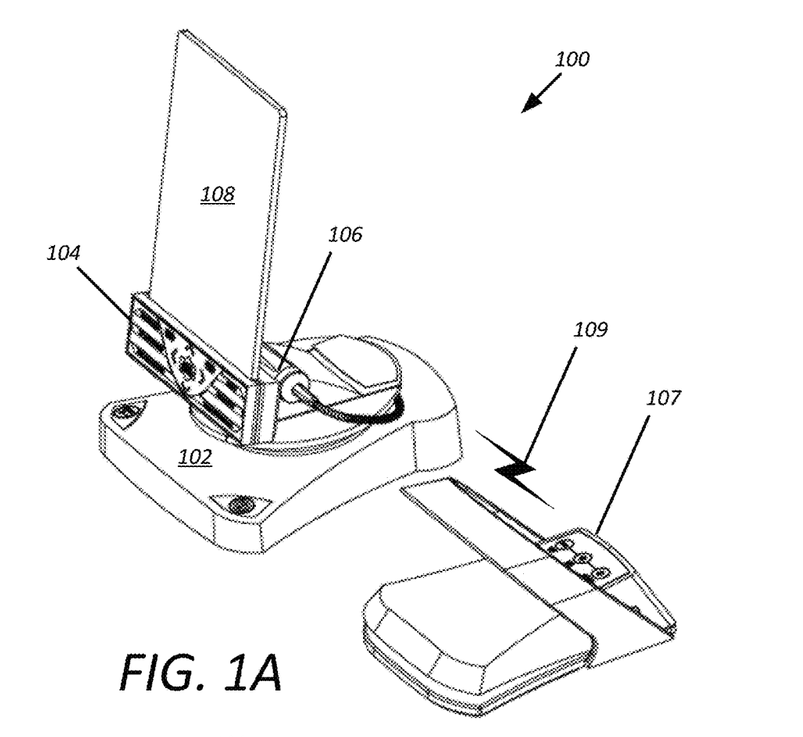
FIG. 1A is a perspective view of an example apparatus constructed in accordance with the present disclosure.

FIG. 1A generally illustrates an example medical apparatus 100 that comprises a housing 102, a laser source 103, a control panel 104 supported on the housing 102, a laser surgical handpiece device 106 coupled to the housing 102, and an electroluminescent display 108. In some embodiments, the apparatus 100 is selectively controlled by use of a foot switch 107. The foot switch 107 can be used to activate and/or deactivate the delivery of electrical energy from the apparatus 100 after the user has set up the apparatus 100. Specifics on setting up the apparatus 100 are provided below. In one embodiment, the foot switch 107 can communicatively couple with the apparatus 100 over a wired or wireless link 109. In some embodiments the foot switch 107 comprises a shroud that prevents accidental laser activation.

The housing 102 comprises the controlling circuitry that powers and operates aspects of the laser source 103 and the electroluminescent display 108.

In some embodiments, the laser surgical handpiece device 106 is coupled with the laser source using a cable that shields and protects a fiber optic (or other) laser guide medium.

Figure 1B:
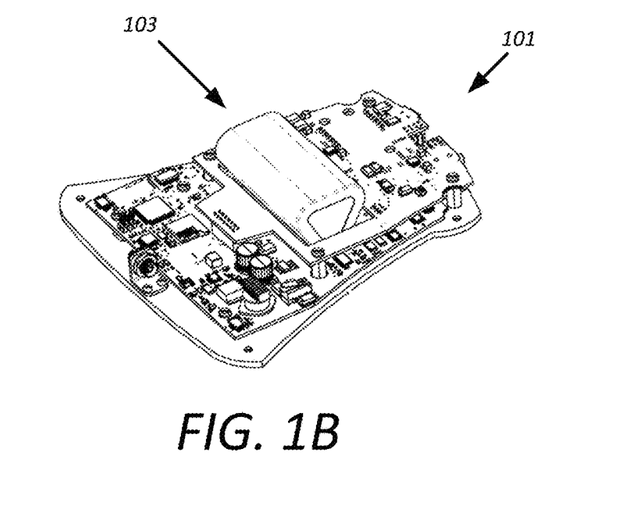
FIG. 1B is a perspective view of an example printed circuit board for use in accordance with the apparatuses of the present disclosure.

In some embodiments, as illustrated in FIG. 1B, the laser source 103 comprises a laser diode module that generates electrical energy that is delivered through an optical cable to the laser surgical handpiece device 106, which is described in greater detail infra. The laser source 103 can be mounted onto a printed circuit board 101 that also comprises the microprocessors, power supplies, and other circuit components of the apparatus 100. The laser diode module 103 is selected from any suitable laser diode module that is capable of producing laser output that is sufficient to perform the medical procedures described herein.

Figure 2A:
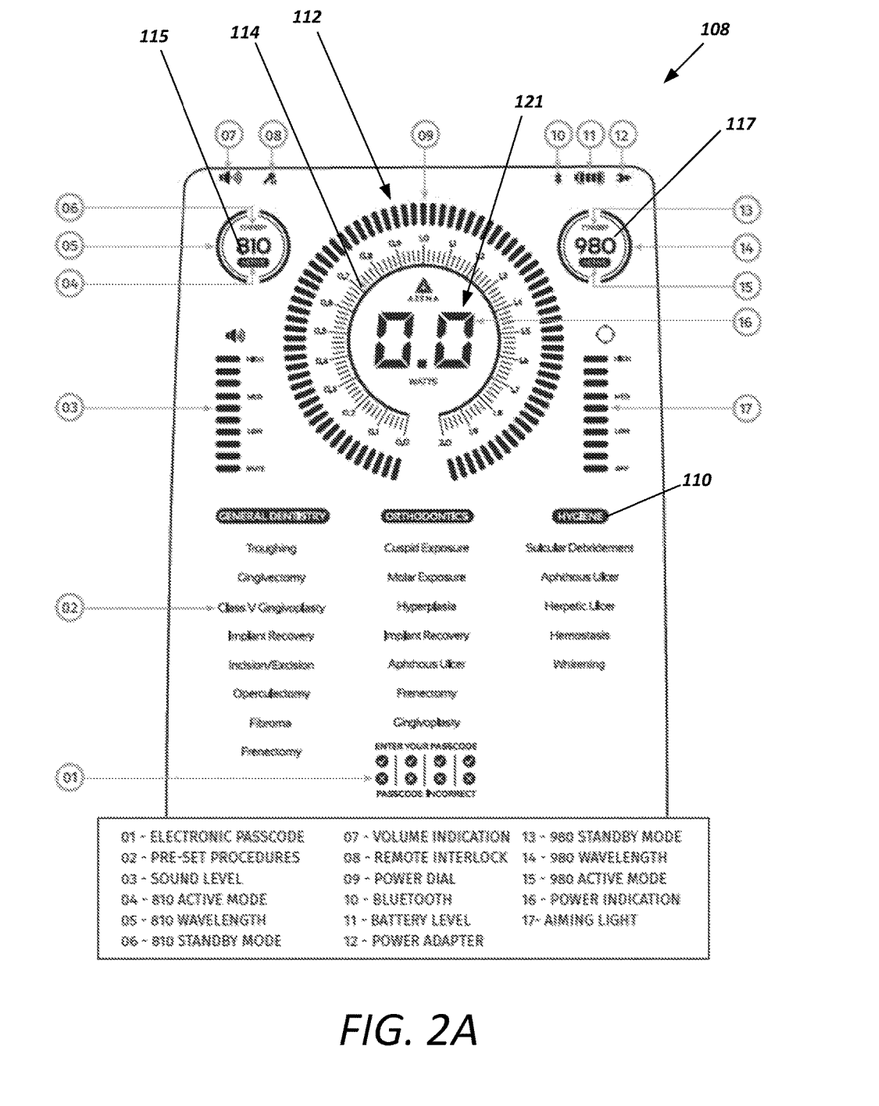
FIG. 2A is a schematic view of an example electroluminescent display of the present disclosure.
Figure 2B:
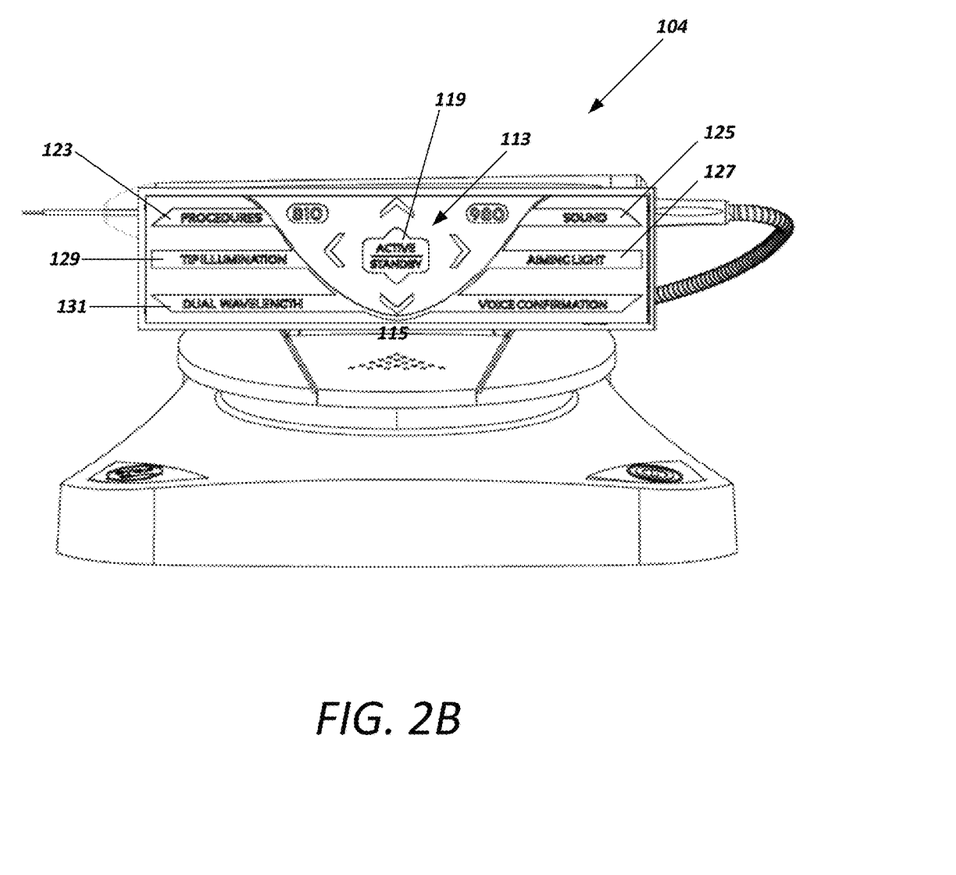
FIG. 2B is an example control panel used to control the apparatus and display of FIGS. 1A and 2A.

FIG. 2A illustrates the electroluminescent display 108 in greater detail. FIG. 2B illustrates an example control panel used to select operational aspects of the apparatus 100. FIGS. 2A and 2B are collectively referred to in the paragraphs below.

The electroluminescent display 108 can include an at least partially transparent display that illustrates various operational modes for the medical apparatus 100. In some embodiments, the medical apparatus 100 can provide the user with lists of selectable operational modes 110 organized into categories such as general dentistry, orthodontics, and hygiene. Each of these categories can include individual operational modes such as troughing, fibroma, and so forth. The operational modes will correspond to a specific setting or group of settings that control how the medical apparatus 100 operates. Again, this can include power and/or laser pulse settings. In some embodiments, the operational modes can be listed and ranked according to power level.

In some embodiments the display 108 is comprises a unique transparent electroluminescent area that can provide extremely high resolution viewing angles from up to 170 degrees of field of view. The display 108 in some embodiments comprises a substrate material having over 80% transparency and an arched configuration of 32 degrees for optimal viewing angle from any direction (other configurations are also likewise contemplated). Illumination of the display 108 is generated by a thin film, less than a micron thick, of specially designed electroluminescent phosphor, which is described in greater detail with respect to FIG. 3B.

In more detail, the apparatus 100 can implement an electronic key passcode. When the user turns the apparatus on, the passcode key screen will be displayed at the bottom center of the display 108. The correct passcode sequence should be entered on the control panel 104 as illustrated and described in FIGS. 2A and 2B collectively. For example the passcode can include a series of directional arrow inputs on a navigation pane 113 of the control panel 104.

When the apparatus 100 is turned on, and the electronic passcode is properly input the apparatus 100 prompts the user with voice confirmation "Please select wavelength" and two flashing wavelength rings 115 and 117 to select the desired wavelength of choice. The apparatus 100 can operate in three wavelength modes: 810 nm alone, 980 nm alone, or dual wavelength. A wavelength mode is selected before proceeding further, but may be changed at any time.

In some embodiments, the laser source 103 of the apparatus 100 can output up to a maximum of 2.0 Watts of average power. To adjust the power setting manually, the user can touch the UP and DOWN or the LEFT and RIGHT arrows on the control panel 104. Each touch of an arrow raises or lowers the power level by 0.1 watts (other increments can be used). Touching and holding an arrow will increase the speed in which the power level is raised or lowered. The user touches the button 119 to put the laser in active mode and depress the foot switch 107 (see FIG. 1) to activate the laser source 103.

The ACTIVE/STANDBY button 119 selection serves a dual purpose. It activates (ACTIVE) and deactivates (STANDBY) the laser. By default, the system powers up in Standby mode. The laser source 103 cannot be activated prior to selecting a wavelength in some embodiments. Each time the ACTIVE/STANDBY button 119 is touched, the apparatus 100 toggles between Active and Standby modes. There is an audio confirmation (unless voice confirmation is muted), and an icon for either "ACTIVE" or "STANDBY" is displayed near each wavelength indicator. The red aiming beam and tip illumination of the laser surgical handpiece device 106 are visible only when the laser is in Active mode. These features are described in greater detail below. Thus, in some embodiments, the laser surgical handpiece device 106 can output a colored aiming light that provides a pinpoint dot of light in the direction where the tip of the laser surgical handpiece device 106 will impact.

When the apparatus 100 is in Active mode, touching any selection other than UP and DOWN or LEFT and RIGHT will return the apparatus 100 to the Standby mode. When the foot switch 107 is depressed in the Active mode, the outer indicator ring around each wavelength ring 115 and 117 on the display 108 flashes to provide a visual indication that the laser surgical handpiece device 106 is firing. The apparatus 100 can also output an audio beep when the laser surgical handpiece device 106 is being fired. For safety purposes, a laser firing delay of 0.25 seconds can be implemented in order to prevent accidental activation.

In some embodiments a PROCEDURES button 123 is selected to bring up preset or pre-programmed procedures (operational settings) on the display 108. A collection of pre-programmed procedures will be revealed on the display 108. Selecting the LEFT and RIGHT arrows will toggle between GENERAL DENTISTRY, ORTHODONTICS or HYGIENE categories. Selecting the UP and DOWN arrows will toggle between procedures within each category. The corresponding power setting for each procedure is displayed on the central numerical power level value 121 when the procedure is highlighted. In some embodiments, the user can customize settings for the apparatus 100 in order to fine tune pre-programmed procedures and/or select settings de novo. The settings can include individual settings for power, pulse width, and the like.

In some embodiments, users can select volume levels for audible feedback from the apparatus 100 using button 125.

In one embodiment the user can utilize an aiming light button 127 and the navigation pane 113 to activate the aiming light of the surgical handpiece device 106, while a button 129 is used to activate tip illumination of the laser surgical handpiece device 106.

The use of dual wavelength laser light can be selected using button 131.

With respect to specifically programmed operational modes, when a surgeon starts to perform laser procedures for the first time, often it is difficult to know the exact power settings for a particular procedure. Several procedures use different settings and it is almost impossible for the clinician to memorize all power settings, specially, if the clinician performs procedures that broads more than one specialty, such as General Dentistry or Orthodontics.

The apparatus 100 provides a menu with commonly used procedures already pre-programmed with laser power and pulse settings for that particular procedure. The apparatus 100 is also programmed with specialty features which allow different clinicians from different specialties to have access to pre-set procedures. The correct power, pulse, and frequency (e.g., duration) are already loaded into the display.

In one embodiment, the user selects the option "Procedures". When selected, the pre-set procedures menu will be displayed on the electroluminescent display 108. As the user toggles between procedures and specialties, a preview of the power settings is shown on the display for easy reading of power.

A collection of pre-programmed procedures (e.g., operational modes) will be revealed on the display. Selecting the LEFT and RIGHT arrows allows for the user to toggle between GENERAL DENTISTRY, ORTHODONTICS or HYGIENE categories. Selecting the UP and DOWN arrows allows for the user to toggle between procedures within each category. The corresponding power setting for each procedure is displayed on the Power Indicator when the procedure is highlighted.

The user can also manually select a power or operational level rather than selecting a listed operational mode by taping or otherwise touching a power indicator dial 112. In some embodiments, the user can utilize a digital or touch input sliders to selectively adjust luminance of a light source within the laser surgical handpiece device 106, as will be described below with respect to FIG. 4.

In some embodiments, the electroluminescent display 108 is controlled by a plurality of microprocessors that control various segments of the electroluminescent display 108. An example microprocessor is illustrated and described with respect to FIG. 8. In some embodiments, the microprocessors can selectively dim portions of the electroluminescent display 108 to indicate a power level on the power indicator dial 112. For example, a portion of the power indicator dial increments, such as increment 114 are illuminated to a greater extent than remaining increments. By way of example, if troughing is selected as an operational mode, the power indicator dial 112 can brighten indicators that extend to around a power level of 0.07. Indicators above 0.07 are dimmed by the microprocessors compared to the indicators below and equal to 0.07.

The power level is displayed in a central numerical power level value 121 portion of the display 108.

With respect to dimming of the electroluminescent display 108, various sectors of the electroluminescent display 108 are controlled by one or more of the microprocessors.

As background, electroluminescent display technology uses AC current to light up specific segments on a particular display. When a segment is lit, it becomes visible and user can interact with it. However, when user interaction is made with a particular segment, it is difficult to visualize selections or change in settings on the lit display.

In order to make the process simpler and easier for the user to make selections and interact with the display user interface, the present technology provides methods of dimming a particular segment. By dimming one or more segments of the display while simultaneously brightening other segments, light intensity can be selectively changed and the user can visually apprehend the change.

Figure 3A:
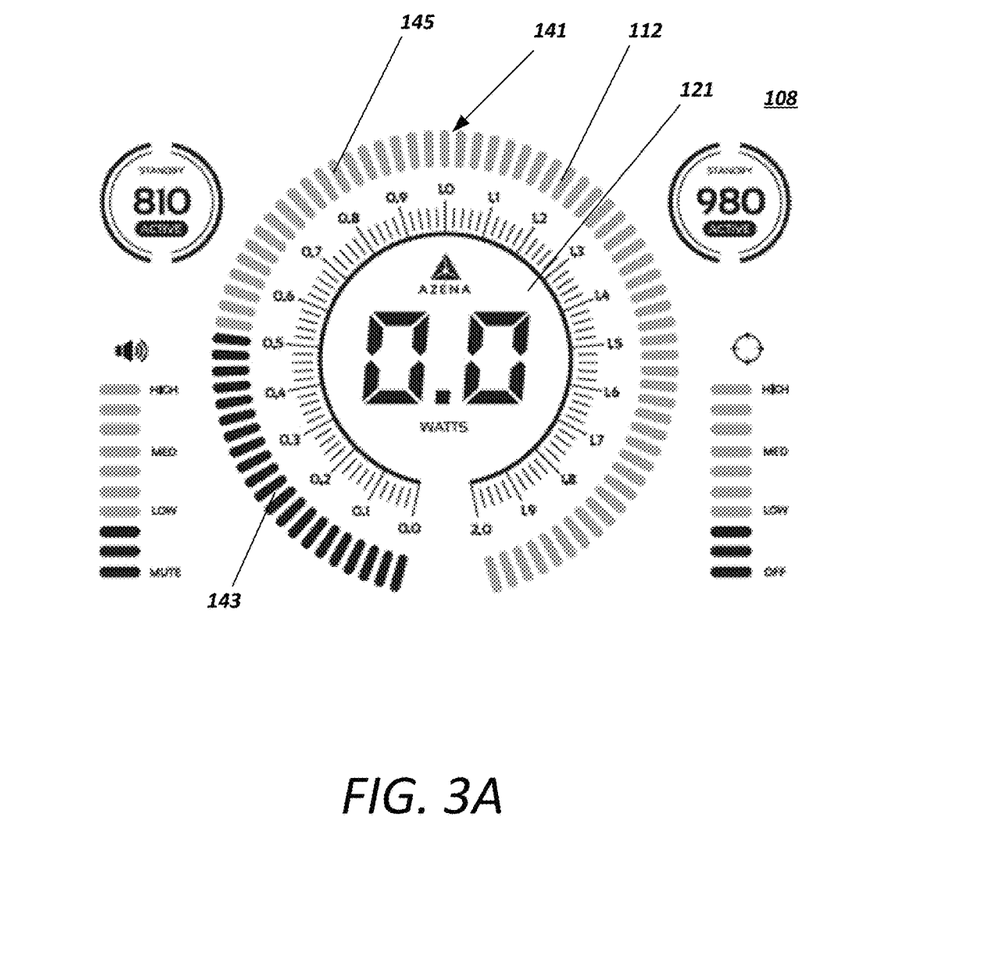
FIG. 3A illustrates a portion of the electroluminescent display that includes a power dial indicator that can receive touch based input.

FIG. 3A illustrates characters or facets, such as increments, of the user interface that are black (indicating full brightness) and some that are light gray (dimmed). The arch reflects a change when user selects an option to increase power where the segment changes from dimmer to full brightness, demonstrating to the user this particular selection was made. The central numerical power level value 121 portion of the display 108 is located within the power indicator dial 112. The dial 112 comprises power indicator dial increments 141 that ring the central numerical power level value 121. Portions of the power indicator dial increments 141, such as portion 143, can be illuminated at a power level that is greater than a power level used to illuminate portion 145 of the power indicator dial increments 141.

Electroluminescent technology requires an AC form of energy to be applied to the segments to produce light. The microprocessors for the electroluminescent display 108 apply a positive and negative pulse at a specific voltage, at a certain frequency, which causes one or more segments to be illuminated. Each pulse can be delivered at a certain pulse width, but the total period of the positive and negative pulse can be adjusted.

Increasing or decreasing the total period of the pulses, changes the frequency and causes the segment to be brighter or dimmer (a differential change in luminance).

The microprocessors change dimming on each display segment by increasing or decreasing a frequency of energy pulsing through a pulse skipping scheme. The pulse skipping scheme allows for pulses to be skipped in the subsequent cycles, which in turn changes the frequency of energy pulses resulting in segments being dimmer as more pulses are skipped.

Stated otherwise, the microprocessors cause illumination of light emitting nodes integrated into the display that provide light to the power indicator dial 112, as well as other display features. In order to provide dimming of these light emitting nodes in the sectors, the microprocessors can be configured to skip or pulse power to light emitting nodes that are selected for dimming relative to the light emitting nodes that are selected to be illuminated. It will be understood that the microprocessors can address individual light emitting nodes, which function similarly to a pixel of a video display. Thus, each light emitting node can be addressed using a channel. The microprocessors can pulse energy to individual light emitting nodes using these dedicated channels. The channels can also be referred to as an electrical trace. The traces extend in vertical lines within the electroluminescent display 108.

The microprocessors can be configured to maintain an energy pulse rate for the light emitting nodes that are selected to be illuminated and then pulse the light emitting nodes that are selected to be dimmed on a schedule, such as only every sixth cycle. One of ordinary skill in the art will appreciate that other pulse schedules and cycles can be utilized based on the desired luminescence differential between illuminated light emitting nodes and dimmed light emitting nodes.

Figure 7:
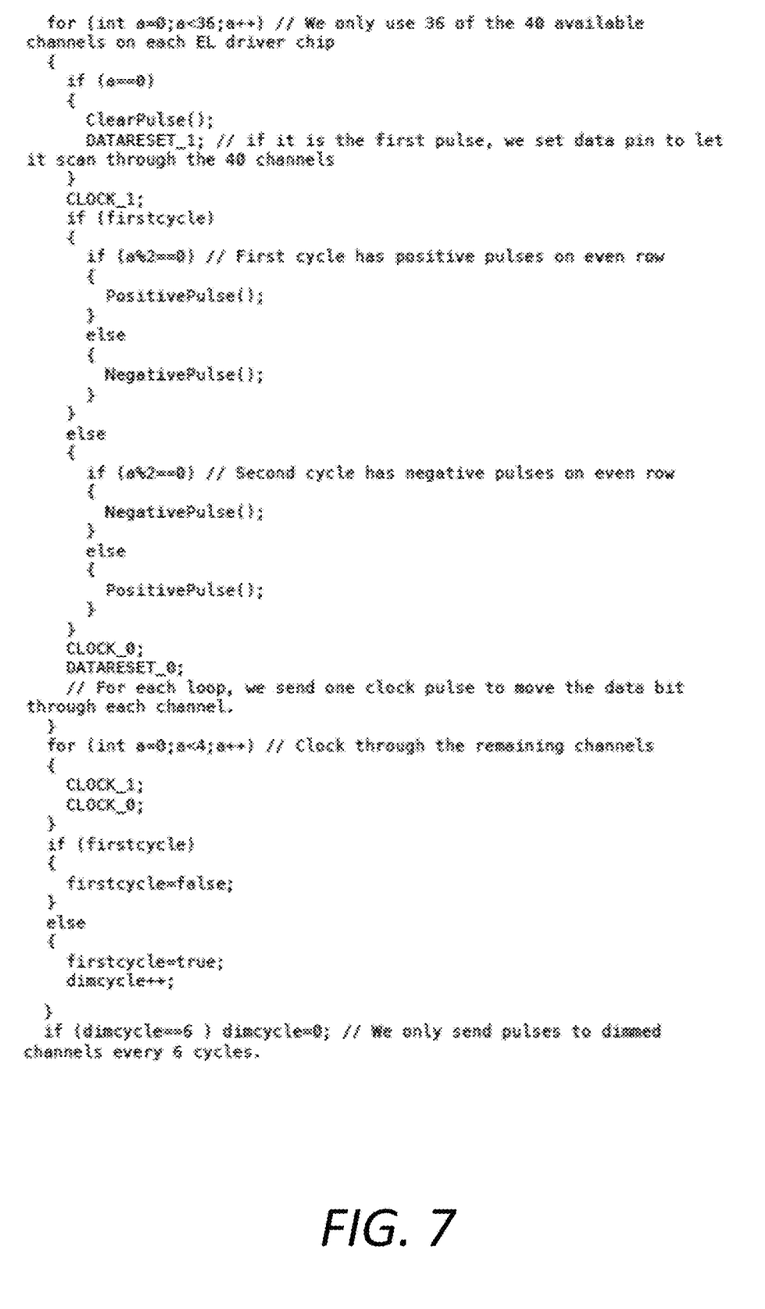
FIG. 7 discloses example code that is used to implement various electroluminescent display control methods.

Example code/instructions that can be executed by the microprocessors for the electroluminescent display 108 to selectively dim the electroluminescent display 108 are found in FIG. 7.

Figure 3B:
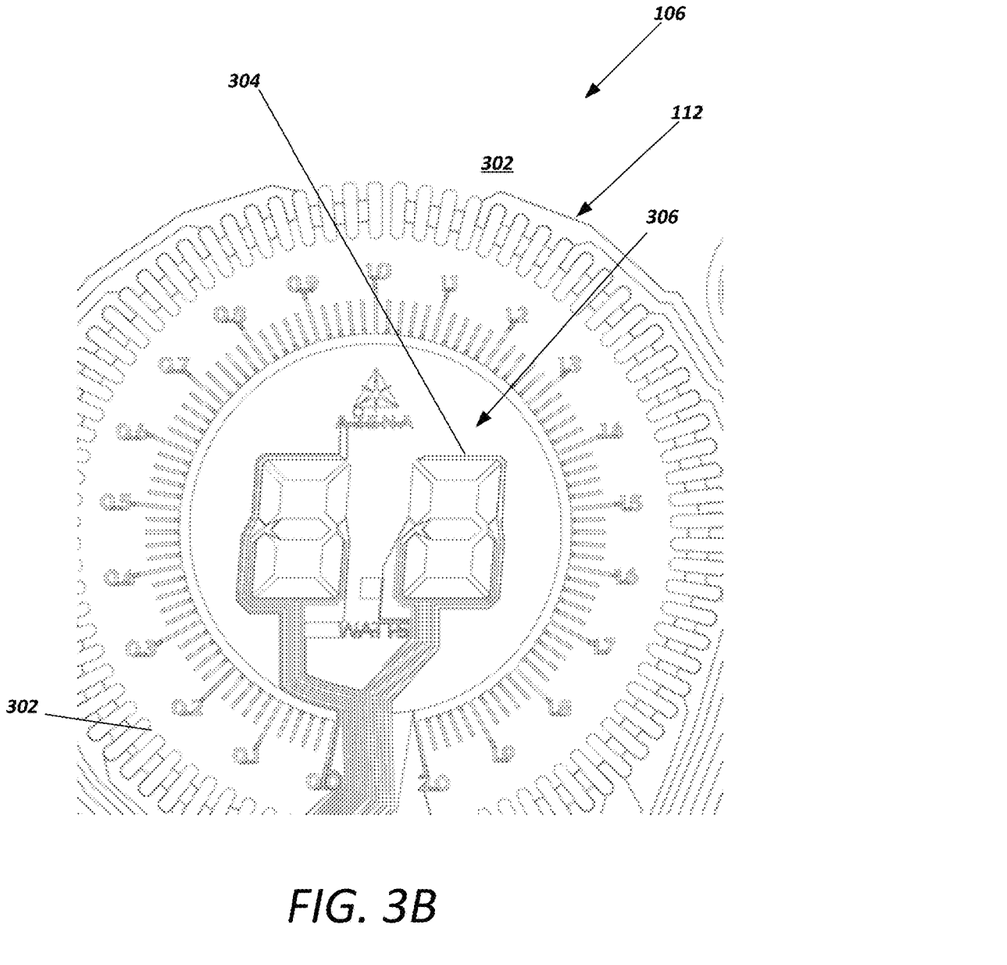
FIG. 3B illustrates a portion of the electroluminescent display having traces and light emitting segments.

FIG. 3B illustrates a section of the electroluminescent display 108. In one embodiment, the electroluminescent display 108 is constructed from a glass substrate 302. To create luminescent segments a plurality of trace lines, such as trace line 304, are formed on the electroluminescent display 108 through deposition of a material such as indium tin oxide or other conductive material. The traces can be formed by the masking of the glass substrate 302 to create GUI elements, such as the power indicator dial 112 or other characters/icons that are to be illuminated. In some embodiments, portions of the traces that correspond to the characters/icons are coated with a material that illuminates when an electrical charge is applied. For example, the trace lines that form the power level digits 306 are covered or coated with phosphor compound. When an electrical charge is applied to the traces by the microprocessors the phosphor produces light.

Thus, the terms "light emitting segment" refers to a portion of a trace that comprises the luminescent material, such as phosphor.

Figure 4:
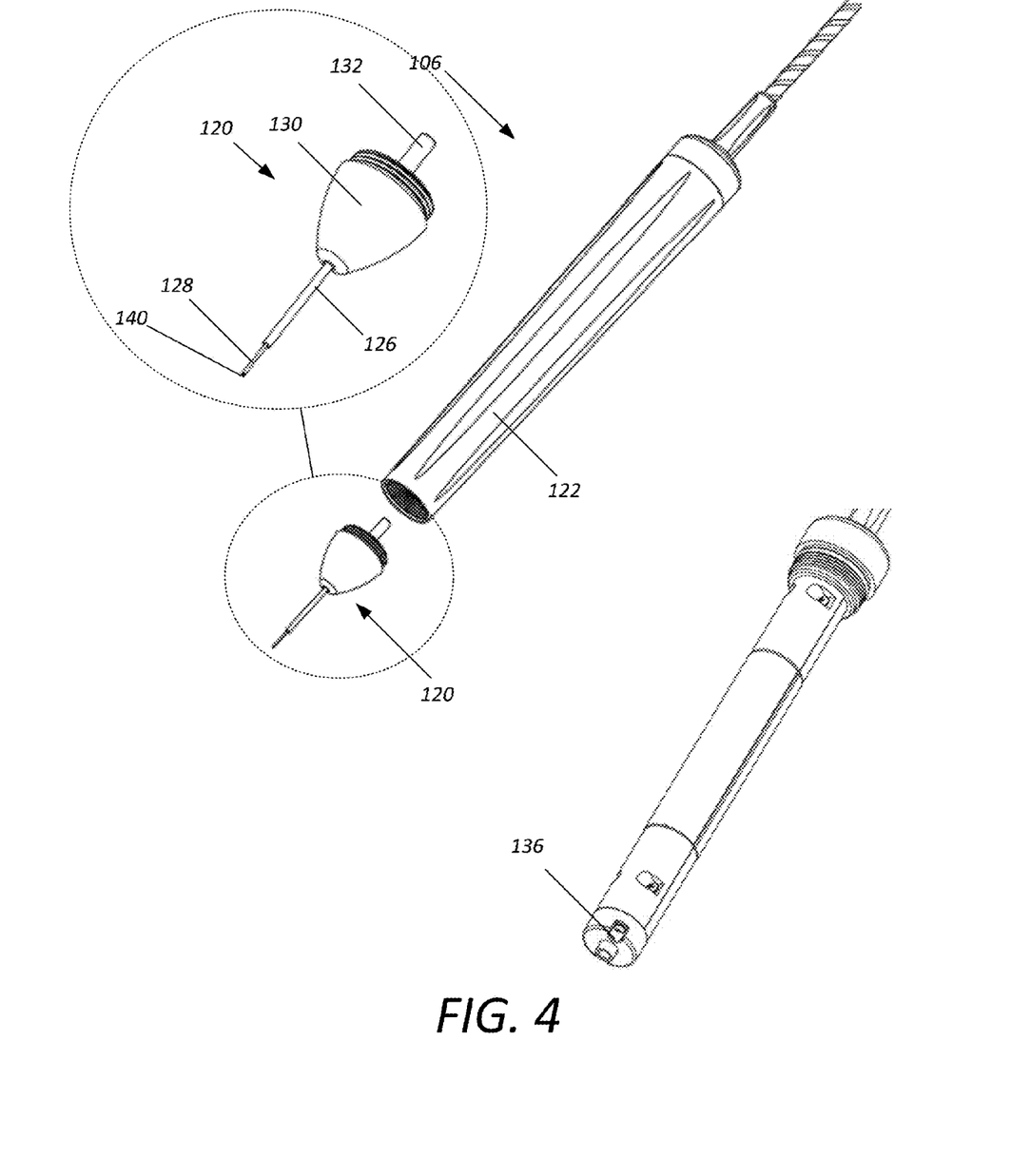
FIG. 4 illustrates several views of a laser handle device of the present disclosure.

As mentioned above, a tip of the laser surgical handpiece device 106 can be illuminated. When performing surgical oral procedures, one of the most difficult challenges is visibility for the clinician. Often times, when procedures are performed in the back of the oral cavity it presents an additional set of challenges to the oral surgeon, as the lack of light decreases the surgical site visibility making it more difficult for the surgeon.

In order to improve site visibility and efficacy during an oral surgical procedure, we have created a transparent disposable tip that hosts a set of LED lights for proper illumination of the oral cavity. This disposable tip holds an optical fiber which delivers electrical energy during the surgical procedure. Because the disposable tip is transparent, it allows the LED light to pass thru and illuminate the surgical site.

A plastic sleeve holds the electronics for the LED which attaches to an aluminum hand piece. This aluminum hand piece threads into the plastic securing the LED system in place. The disposable tip threads into the aluminum piece just in front of the LED. Because the disposable tip is transparent, it allows light to pass through making this surgical handle become similar to a flashlight.

FIG. 4 illustrates an example laser surgical handpiece device 106 that comprises an interchangeable/disposable tip 120 and a tubular body 122. The tip 120 comprises a sheath tip 126, a fiber optic conduit 128 extending through the sheath tip 126, a light emitting cap 130, and an optical ferrule 132. The light emitting cap 130 can comprise an at least partially transparent plastic material that allows light emitted by a light source 136, such as an LED to pass through and illuminate an area forward of the sheath tip 126 and fiber optic conduit 128. In one embodiment, an LED is coupled with a light source 136 and positioned within the tubular body 122. The optical ferrule 132 directs light emitted by the light source into the fiber optic conduit 128.

According to some embodiments, the light source 136 can be selectively controlled from the control panel 104 to selectively adjust a luminance of the least partially transparent tip. That is, the light emitted by the light source 136 can be adjusted by the end user to a desired luminance level.

In some embodiments the interchangeable/disposable tip 120 comprises fiber tip 140 that is pre-initiated with a pigment. In some embodiments a black pigment is added to the end of each fiber tip to help focus electrical energy at the tip. Procedures that require removal or cutting of soft tissue can employ an initiated tip, whereas some procedures that call for an un-initiated tip, such as Aphthous Ulcer treatment where no tissue is being removed, do not require a pre-initiated lip. When a procedure calls for an uninitiated tip, the user can rub off the pigment at the end of the fiber tip 140 with gauze and isopropyl alcohol. Again, not all soft-tissue procedures require an initiated, or darkened, tip and contact with tissue. Those procedures that do not require tissue contact will use a fiber tip that is not initiated, because to be effective in non-contact mode, electrical energy must flow unimpeded from the tip into the target tissues. While the above sections describe the specific components and construction of example apparatuses of the present disclosure, the following sections describe example methodologies that relate to the use and/or operation of example apparatuses of the present disclosure.

Figure 5:
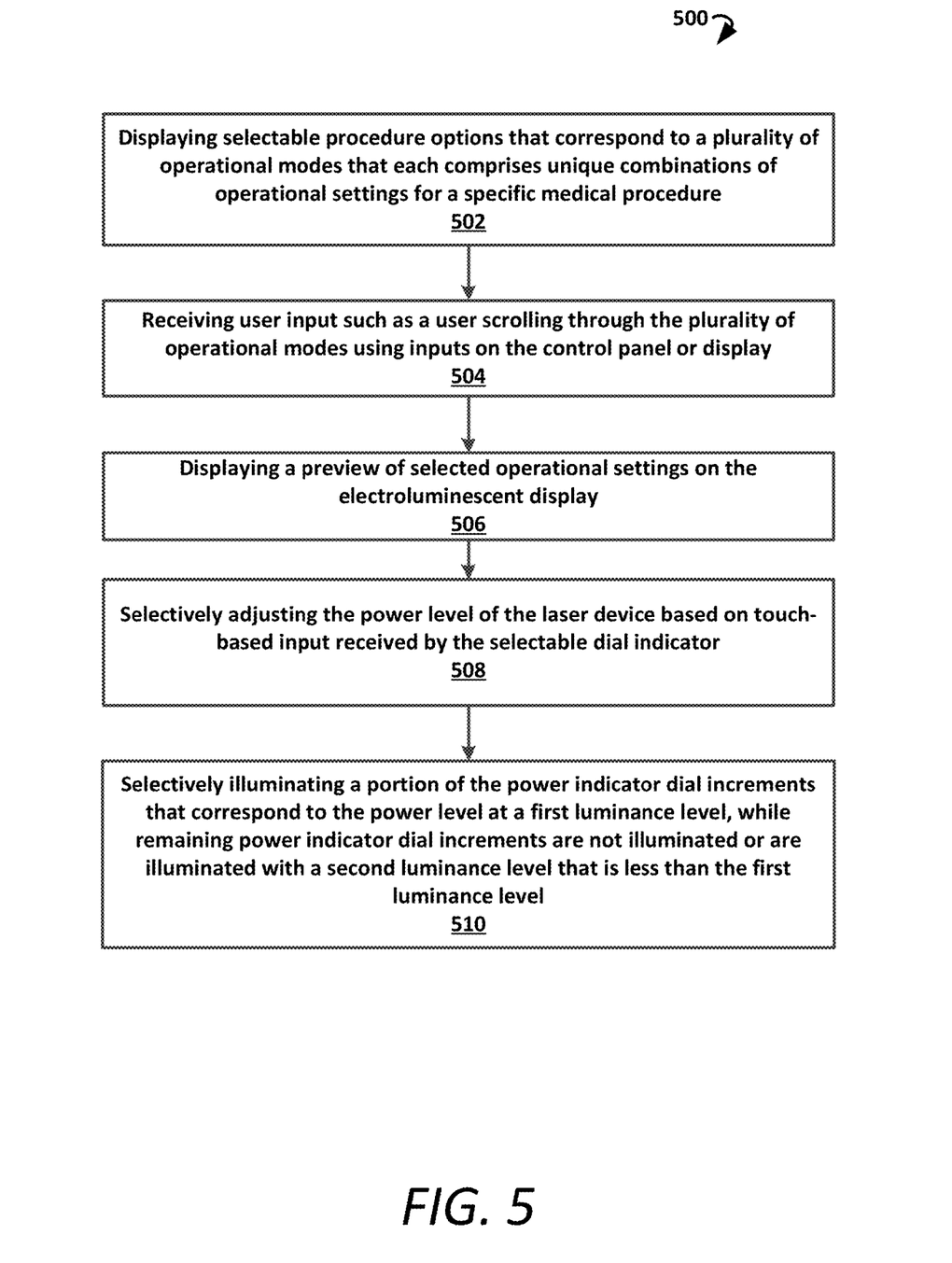
FIG. 5 is a flowchart of an example method of controlling an electroluminescent display of the present disclosure.

FIG. 5 is a flowchart of an example method 500 executed by the microprocessor of the present disclosure. In one embodiment, the method includes a step 502 of displaying selectable procedure options that correspond to a plurality of operational modes that each comprises unique combinations of operational settings for a specific medical procedure. The plurality of operational modes and pre-configured settings are displayed on the electroluminescent display.

The method further comprises a step 504 of receiving user input such as a user scrolling through the plurality of operational modes using inputs on the control panel (or in a selectable dial indicator displayed on the electroluminescent display). In response, the method includes a step 506 of displaying a preview of selected operational settings on the electroluminescent display.

In one embodiment, the power level of the operational settings is displayed within a selectable dial indicator displayed on the electroluminescent display.

When selected, the method further includes a step 508 of selectively adjusting the power level of the laser source based on touch-based input received by the selectable dial indicator. This allows a user to fine tune device settings if the user desires to change any of the selected operational settings. Thus, the operational settings provide generalized, procedure-based settings; the user can then fine tune these operational settings for the patient.

In some embodiments, the selectable dial indicator comprises power indicator dial increments that ring a central numerical power level value display. These dial increments are selectable by the user to set or fine tune a power level.

When the user has chosen selected operational settings for the apparatus, the method includes a step 510 of selectively illuminating a portion of the power indicator dial increments that correspond to the power level at a first luminance level, while remaining power indicator dial increments are not illuminated or are illuminated with a second luminance level that is less than the first luminance level.

Figure 6:
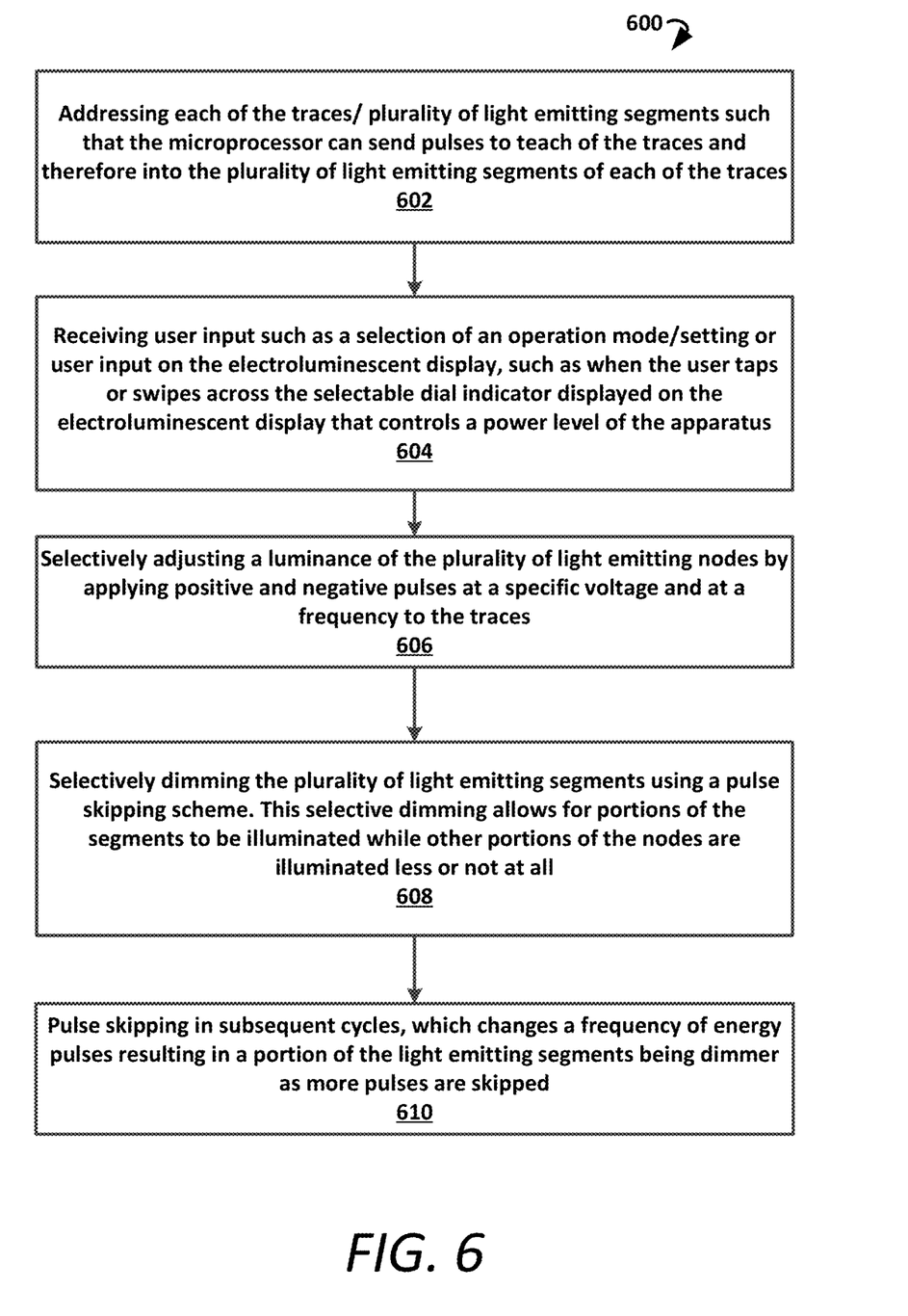
FIG. 6 is a flowchart of another example method of controlling an electroluminescent display of the present disclosure.

FIG. 6 is a flowchart of an example method 600 for controlling an electroluminescent display. For context, the electroluminescent display is comprised of a plurality of light emitting segments. In some embodiments groups of light emitting segments are arranged in lines within the electroluminescent display. These lines form characters, icons, or other representations of the display.

The light emitting segments comprise portions of the traces that have a luminescent coating (such as phosphor). In some embodiments, each of the traces is addressed to the microprocessor.

In one embodiment, the method comprises a step 602 of addressing each of the traces such that the microprocessor can send pulses to each of the traces and therefore into the plurality of light emitting segments of each of the individual traces.

The method comprises a step 604 of receiving user input such as a selection of an operation mode/setting or user input on the electroluminescent display, such as when the user taps or swipes across the selectable dial indicator displayed on the electroluminescent display that controls a power level of the apparatus.

Thus, the electroluminescent display can comprise a touchscreen layer that is constructed from suitable touchscreen display technology that would be known to one of ordinary skill in the art with the present disclosure before them.

In one embodiment, the method includes a step 606 of selectively adjusting a luminance of the plurality of light emitting segments by applying positive and negative pulses at a specific voltage and at a frequency to the traces that correspond to the light emitting segments that are to be adjusted. As mentioned above, the positive and negative pulses have a selected pulse width, further wherein a length of the positive and negative pulses are selectively adjusted by the microprocessor.

In some embodiments, the positive and negative pulses of electrical energy have a fixed pulse width and an adjustable frequency. In one or more embodiments, a period of the positive and negative pulses are selectively controlled by a microprocessor, which effectively changes the frequency of the electrical energy pulses.

The method includes a step 608 of selectively dimming the plurality of light emitting segments using a pulse skipping scheme. This selective dimming allows for portions of the segments to be illuminated while other portions of the segments are illuminated less or not at all. Again, the power level for a portion of the segments is set at a first luminance level, while other segments are not illuminated or are illuminated with a second luminance level that is less than the first luminance level.

According to some embodiments, the method includes a step 610 of pulse skipping in subsequent cycles, which changes a frequency of energy pulses resulting in a portion of the light emitting segments being dimmer as more pulses are skipped.

As used herein, the term "engine", "system", "client", "module", "controller or microprocessor", or "application" may also refer to any of an application-specific integrated circuit ("ASIC"), an electronic circuit, a processor (shared, dedicated, or group) that executes one or more software or firmware programs, a combinational logic circuit, and/or other suitable components that provide the described functionality.

Figure 8:
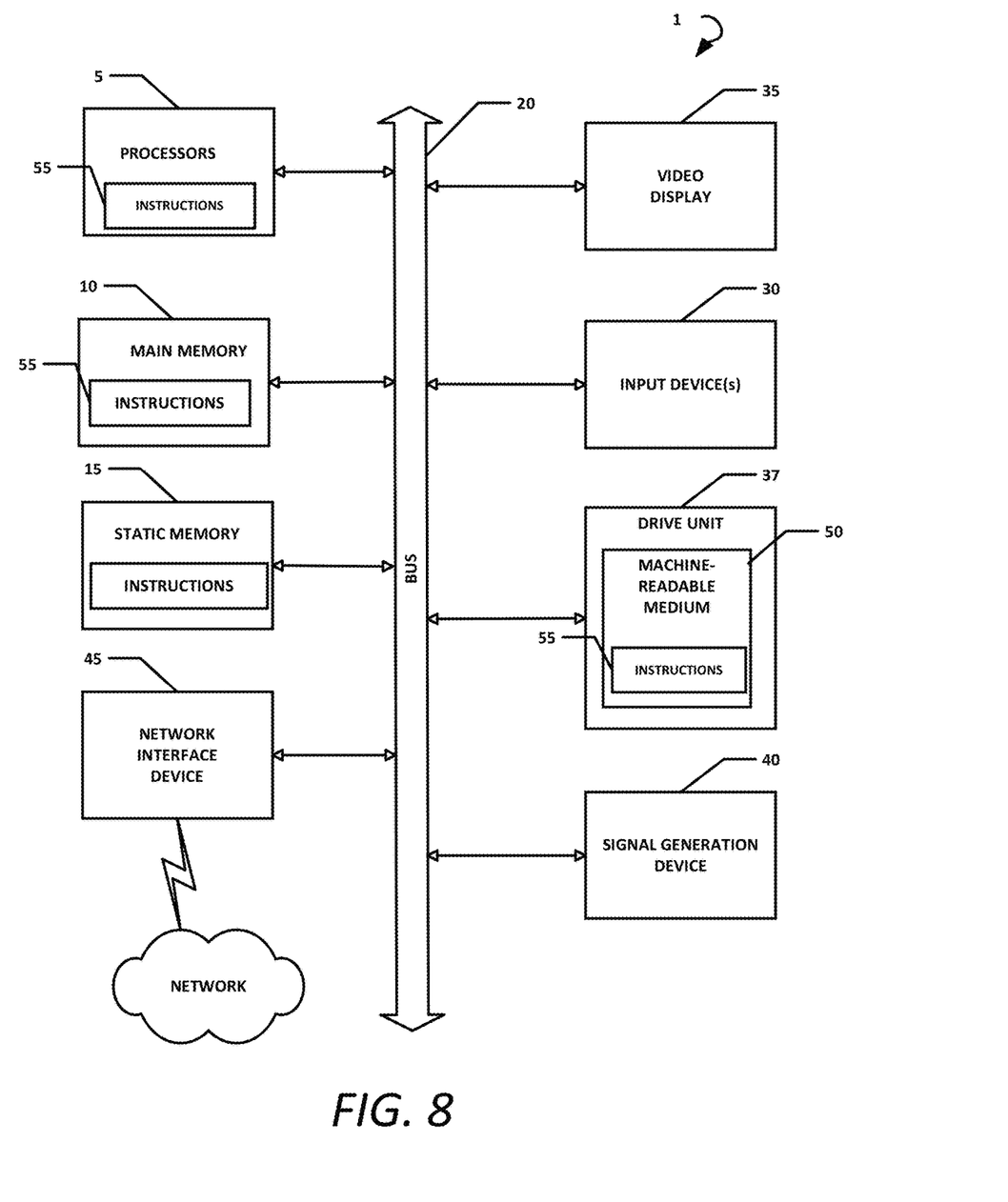
FIG. 8 is a schematic of an example computing device, all or portions of which can be used to practice aspects of the present disclosure.

FIG. 8 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a robotic construction marking device, a base station, a personal computer (PC), a tablet PC, a set-top box (STB), a personal digital assistant (PDA), a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1 includes a processor or multiple processors 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alphanumeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processors 5 during execution thereof by the computer system 1. The main memory 10 and the processors 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

Not all components of the computer system 1 are required and thus portions of the computer system 1 can be removed if not needed, such as Input/Output (I/O) devices (e.g., input device(s) 30). One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present technology. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Bolt") may be interchangeably used with its non-capitalized version (e.g., "bolt"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "mechanically connected," etc., are used interchangeably herein to generally refer to the condition of being mechanically/physically connected. If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, extrusion, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

Additionally, components described as being "first" or "second" can be interchanged with one another in their respective numbering unless clearly contradicted by the teachings herein.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

What is claimed is:

1. An apparatus, comprising:
   a housing;
   a laser surgical handpiece device;
   a laser source that generates laser light that is emitted through the laser surgical handpiece device;
   an electroluminescent display associated with the housing, the electroluminescent display being configured to display operational settings for the laser source, the electroluminescent display comprising a plurality of rows of traces, which are each spaced apart from one another across a glass substrate and are used to illuminate characters of the electroluminescent display; and
   a microprocessor for controlling the electroluminescent display using a pulse skipping scheme applied to the plurality of rows of traces so as to selectively display the operational settings and to maintain an energy pulse rate for the illuminated characters.

2. The apparatus according to claim 1, further comprising a control panel disposed under the electroluminescent display, the control panel comprising inputs for selecting a power level, a pulse width, and a duration.

3. The apparatus according to claim 1, further comprising a fiber optic cable that couples the laser surgical handpiece device with the laser source located within the housing.

4. The apparatus according to claim 1, wherein the microprocessor is configured to provide a plurality of operational modes that each comprise unique combinations of operational settings for a specific medical procedure, the settings being pre-configured, the pre-configured settings being displayed as selectable procedure options on the electroluminescent display.

5. The apparatus according to claim 4, wherein as a user scrolls through the plurality of operational modes, a preview of the operational settings are displayed on the electroluminescent display.

6. The apparatus according to claim 5, wherein a power of the operational settings is displayed within a selectable dial indicator displayed on the electroluminescent display.

7. The apparatus according to claim 6, further comprising selectively adjusting the power of the laser source based on touch-based input received by the selectable dial indicator displayed on the electroluminescent display.

8. The apparatus according to claim 6, wherein the selectable dial indicator comprises power indicator dial increments that ring a central numerical power level value display.

9. The apparatus according to claim 8, wherein controlling the electroluminescent display comprises selectively illuminating a portion of the power indicator dial increments that correspond to a power level at a first luminance level, while remaining power indicator dial increments are not illuminated or are illuminated with a second luminance level that is less than the first luminance level.

10. The apparatus according to claim 9, wherein the microprocessor can selectively adjust a luminance of a portion of a plurality of rows of traces by applying the pulse skipping scheme comprising positive and negative pulses to the portion of the plurality of rows of traces at a specific voltage and at a frequency so as to illuminate only a portion of the plurality of rows of traces required to display the characters associated with the power level and a pulse width or duration.

11. The apparatus according to claim 10, wherein the positive and negative pulses have a fixed pulse width and an adjustable frequency, further wherein a period of the positive and negative pulses are selectively controlled by the microprocessor, which effectively changes the frequency.

12. The apparatus according to claim 10, wherein the plurality of rows of traces each comprise a conductive material that is deposited on the glass substrate of the electroluminescent display, wherein the conductive material is at least partially coated with a phosphor that illuminates when an electrical charge is applied.

13. The apparatus according to claim 10, wherein the microprocessor selectively dims a second portion of the plurality of traces using a pulse skipping scheme.

14. The apparatus according to claim 13, wherein the pulse skipping scheme allows for pulse skipping in subsequent cycles, which changes a frequency of energy pulses resulting in the second portion of the traces being dimmer as more pulses are skipped.

15. The apparatus according to claim 1, wherein the laser surgical handpiece device comprises:
a handle; and
a light source disposed within the handle.

16. The apparatus according to claim 15, further comprising an at least partially transparent tip that emits light from the light source, the at least partially transparent tip comprising a centrally located fiber that emits laser output of the laser source, wherein the light source is controlled so as to selectively adjust a luminance of the least partially transparent tip.

17. The apparatus according to claim 16, further comprising a fiber optic conduit and an optical ferrule that directs light emitted by the light source into the fiber optic conduit and towards the at least partially transparent tip.

18. The apparatus according to claim 17, wherein a tip of the at least partially transparent tip is pre-initiated with pigment to focus electrical energy.

19. An apparatus, comprising:
a housing;
a laser surgical handpiece device;
a laser source that generates laser light that is emitted through the laser surgical handpiece device;
an electroluminescent display associated with the housing, the electroluminescent display being configured to display operational settings for the laser source, the operational settings comprising at least power level and pulse width or duration; and
a microprocessor for controlling the electroluminescent display to selectively illuminate or dim at least a portion of the operational settings thereon based on the operational settings selected by a user, the microprocessor selectively adjusts a luminance of a plurality of light emitting segments by applying positive and negative pulses to an associated trace at a specific voltage and at a frequency.

* * * * *